US00PP17655P2

(12) United States Plant Patent
Barbour

(10) Patent No.: US PP17,655 P2
(45) Date of Patent: Apr. 24, 2007

(54) CHINESE ELM TREE NAMED 'BSNUPF'

(50) Latin Name: *Ulmus parvifolia*
Varietal Denomination: BSNUPF

(75) Inventor: John Hinds Barbour, Monroe, GA (US)

(73) Assignee: Athena Trees, Monroe, GA (US)

( * ) Notice: Subject to any disclaimer, the term of this patent is extended or adjusted under 35 U.S.C. 154(b) by 0 days.

(21) Appl. No.: 11/293,406

(22) Filed: Dec. 2, 2005

(51) Int. Cl.
*A01H 5/00* (2006.01)

(52) U.S. Cl. ..... Plt./221
(58) Field of Classification Search ..... Plt./221
See application file for complete search history.

*Primary Examiner*—Kent Bell
*Assistant Examiner*—Annette H Para
(74) *Attorney, Agent, or Firm*—Klarquist Sparkman LLP

(57) ABSTRACT

A Chinese Elm tree named 'BSNUPF' having tight upright narrow growth, tight branches, and ornamental bark that exfoliates in patches to provide patch marks of different colors.

3 Drawing Sheets

Latin name of genus and species: *Ulmus parvifolia.*
Variety denomination: 'BSNUPF'.

BACKGROUND OF THE INVENTION

The present invention relates to a new and distinct variety of *Ulmus parvifolia,* Chinese Elm, which has been given the varietal name 'BSNUPF.'

The original tree of this new Chinese or Lace Bark Elm variety was discovered by the inventor in 1994 as a chance seedling growing in a cultivated area of a nursery in Monroe, Ga. This newly discovered tree was growing in a row of Chinese Elm seedlings in the nursery. This tree was transplanted to an area of the nursery where it could be observed, where it has remained since that time. The original tree is now about 11 years old from a seed. The description of this new Chinese Elm variety is based on observations of this original tree and of asexually propagated progeny, asexually propagated in Monroe, Ga., from softwood cuttings and by budding. This new tree has proven to be capable of reliable asexual propagation using vegetative propagation techniques. These asexually propagated progeny are being grown at a nursery in Oconee County, Ga. Observations of the original tree, and of asexually propagated progeny of this new variety, have proven that the unique combination of characteristics of this new variety as described below are firmly fixed.

Common Chinese Elm can grow up to two times wider than high. One selection that the inventor has observed, namely, Emer I (U.S. Plant Pat. No. 7,551) has branches that spread as the tree grows to result in a globe-shaped tree. Seedling Chinese Elm trees often have ornamental exfoliating bark varying from brown exfoliating shreds to multicolored exfoliated patches, but Chinese Elm trees with exfoliating multi-colored patches in combination with a tight upright narrow growth have not been observed by the inventor.

This new Chinese Elm tree variety is distinguished from other Chinese Elm varieties known to the inventor by the following unique combination of characteristics: its tight upright narrow growth habit, branch angles that remain tight from the bottom to the top of the tree; and ornamental bark that exfoliates in patches to provide patch marks of more than one color.

BRIEF SUMMARY OF THE INVENTION

The original tree of this new Chinese Elm variety has been successfully propagated by softwood cuttings and by budding at my direction. This asexual reproduction was accomplished in Monroe, Ga. The progeny have demonstrated that the novel characteristics of this new variety are fixed, stable, and reproduce true to type through asexual propagation. These observations confirm that 'BSNUPF' represents a new, distinct, and improved variety of Chinese Elm, as particularly evidenced by the combination of characteristics described above (tight upright growth, tight branches, and ornamental bark that exfoliates in patches to leave patch marks of more than one color).

BRIEF DESCRIPTION OF THE DRAWINGS

The accompanying photographs illustrate this new Chinese Elm variety with color as true as reasonable possible in this type of color photograph.

DETAILED BOTANICAL DESCRIPTION

This invention has not been observed under all possible environmental conditions. The phenotype may vary with variations in growing environment, such as temperature, light intensity, day length, rainfall, or nutrient availability, without, however, any variation in genotype. 'BSNUPF' Chinese Elm is currently growing at a nursery in Monroe, Ga.

The following is a detailed description of my new variety of Chinese Elm with color terminology in accordance with The Royal Horticultural Society (R.H.S.) Colour Chart published by The Royal Horticultural Society in London, England. This description is based on observations of the original tree growing at a nursery site in Monroe, Ga.

Parentage: Discovered as a chance seedling of unknown origin growing in a cultivated area of a nursery in Monroe, Ga.

Tree shape: Upright tight narrow with narrow crotch angles. As branches extend with age, the angle of the branch (in relation to the trunk) has not been observed to widen, rather it remains tight. The branches had no noticeable weeping with age over the period of observation.

Size and growth rate: The original tree at nine years of age was 18.5 cm in caliper at 0.3 m above the ground, about 8 m high, and about 2 m wide, thus providing an overall height to width ration of about 4.0. The 185 cm caliper growth over a nine year observation period computes to an average growth in caliper of the original tree of about 2.0 cm per year. The growth rate in height of the tree has been rapid, at slightly less than 1 m per year on average over a nine year observation period.

Figure 1:
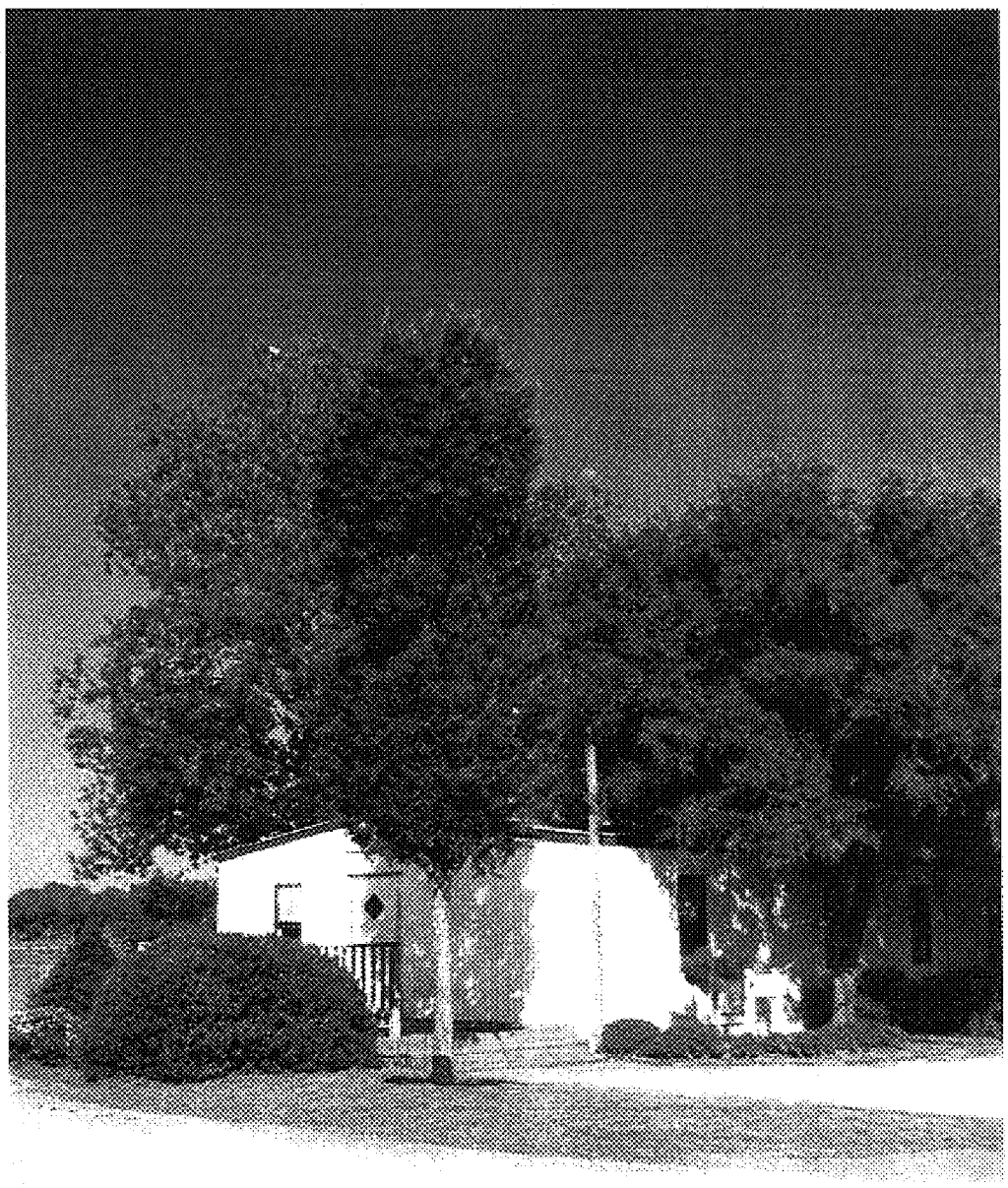
FIG. 1 is a photograph of the original tree (foreground) of the new variety taken in April of 2001 as the tree began to leaf out. The narrow width and tight branching habit of the new tree is apparent in this photograph. A seedling Chinese Elm tree is behind and to the right of the new tree and is much more spreading.
Figure 2:
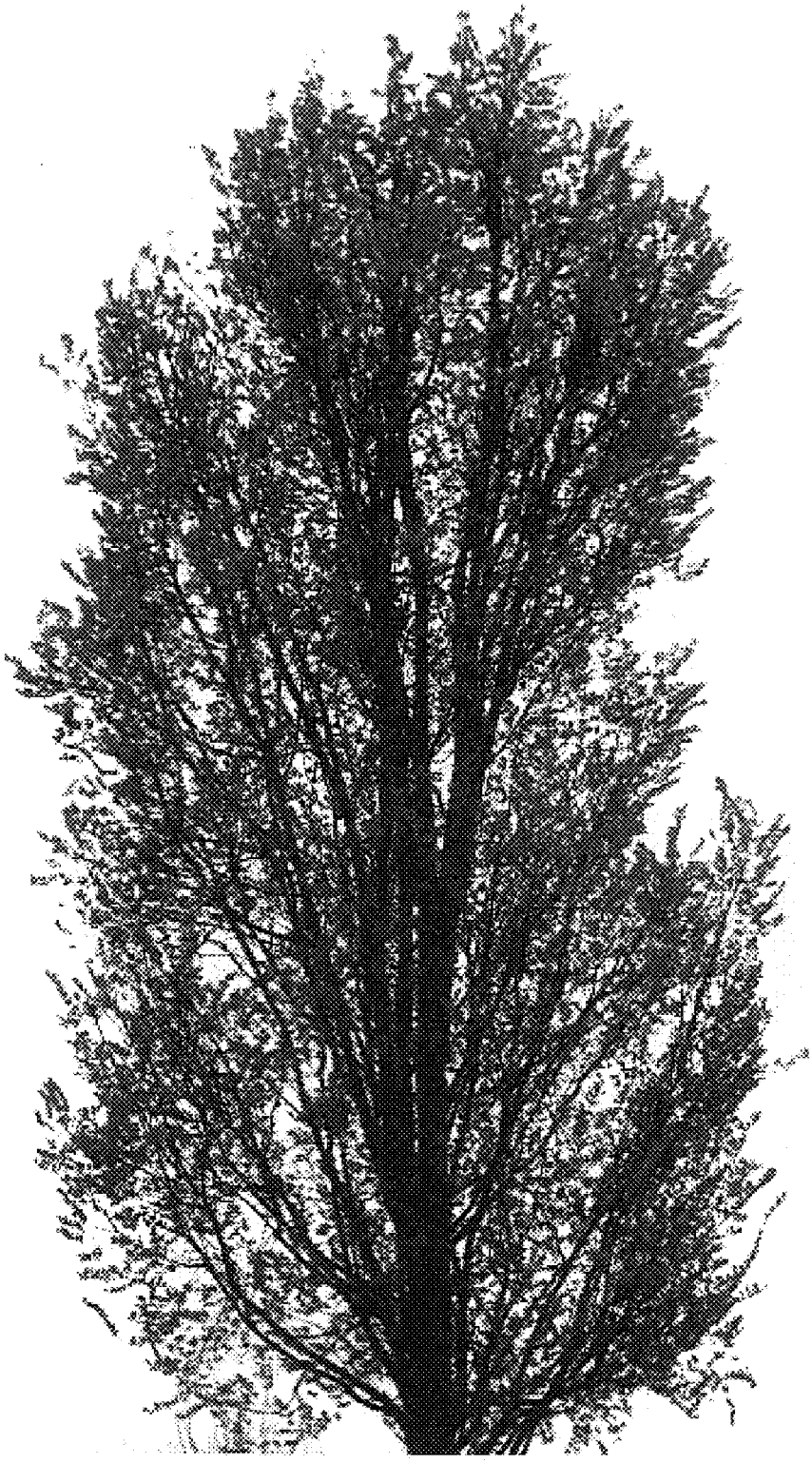
FIG. 2 is a close up photograph of the original tree of the new variety to show the tight branches of this tree.
Figure 3:
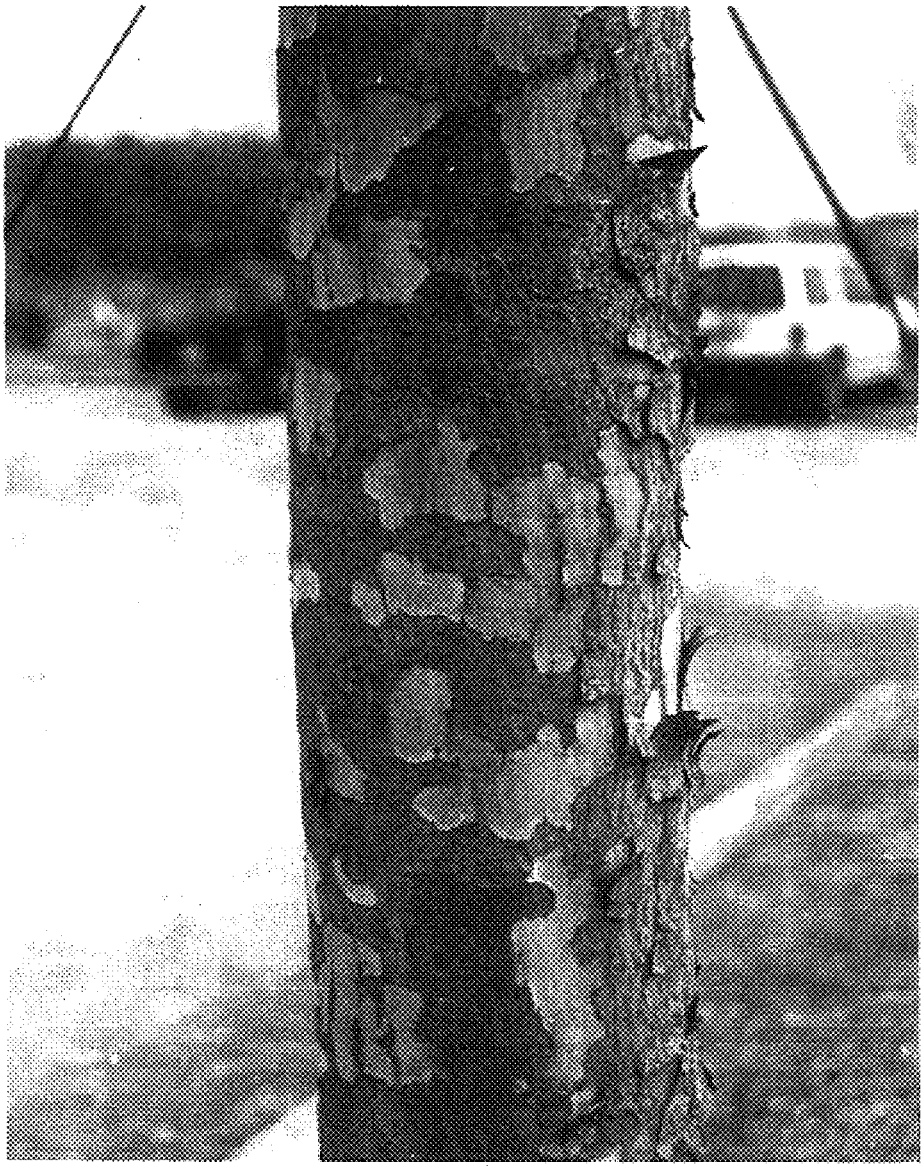
FIG. 3 is a close up photograph of a portion of the trunk of this tree showing the bark exfoliating in patches.

Trunk: Bark is ornamental, exfoliating in camouflage-like patterns of medium to darker and pale gray (RHS Greyed-Green Group 198A, 198C, 197C and 197D) and with the deepest parts of the patterns a bright flesh to orange color (RHS Greyed-Orange Group 173D). On the inside of the exfoliating patches is the same flesh to orange color that is revealed by their curling away from the trunk and vacating the bark. As *Ulmus parvifolia* tress with ornamental bark mature, this feature continues to increase in aesthetic quality (See FIG. 3).

Branching habit: Branching angle is tight and branches stay tight from the bottom to the top of the tree. Taking a typical simple branch and traveling 117 cm up the length of the branch, the branch was only 28 cm from the trunk. Traveling a length of 244 cm up the length of the branch from the trunk, the branch was 51 cm from the trunk, still remarkably tight. Typical branch angle (included angle) from trunk of tree to branch ranges from about ten degrees to about twenty degrees.

Branches:

*Exemplary diameter.*—1.5 mm diameter, 2.50 cm below end bud.

*Surface.*—New growth, medium bright green (RHS Yellow-Green Group 144B) and pubescent with clear hairs; second year, dark flat brown (RHS Grey-Brown Group 199A).

*Pith.*—Solid, uniform.

*Leaf scar.*—Crescent to oval shaped, three bundle traces, typical 2 mm high, 1 mm wide.

*Lenticels.*—Orange (RHS Greyed-Orange Group 168A) lenticels on trunk and stems, oriented vertically.

*Odor.*—None.

Leaves:

*General.*—Deciduous, simple, arranged alternately.

*Shape.*—Elliptic to ovate.

*Margin.*—Serrate.

*Base.*—Oblique.

*Apex.*—Acute.

*Surface.*—Flat dark green, coriaceous, 12 pinnate vein pairs.

*Typical length and width.*—5 cm long, 2.4 cm wide.

*Color.*—Summer: Upper Surface: Flat dark green (RHS Yellow-Green Group 147A). Underside: Flat medium green (RHS Yellow-Green Group 147B). New Leaves: Upper Surface: Bright medium green (RHS Yellow-Green Group 144A). Underside: Flat medium green (RHS Yellow-Green Group 146D). Fall Color: Dull brown (RHS Brown Group 200C) blended with dull yellow (RHS Greyed-Yellow Group 160A) and washed-out green (RHS Yellow-Green Group 146C).

*Petiole.*—Typically six mm long, rounded, rose (RHS Red-Purple Group 70B) on upperside, pale green (RHS Yellow-Green Group 145A) on underside, entire petiole pubescent with clear hairs.

Buds:

*Flower buds.*—Lateral and auxiliary, conical, typically 1 mm high and 1 mm wide, brown (RHS Brown Group 200D), angled toward the trunk, scales imbricate, five scales, with clear thread-like hairs around the margin of each scale.

*Vegetative buds.*—Lateral, oval, typical 1.5 mm high and 1.5 mm wide, brown (RHS Brown Group 200D), scales imbricate, three scales, with clear thread-like hairs around the margin of each scale.

Flowers:

*Overall description.*—Inconspicuous, typical flower is 3 mm high, 2 mm wide, perfect, 4 stamens, 1 pistil, 4 petals, born in fascicles of 4 to 5.

*Petals.*—4 each typically 1.5 mm high and 1 mm wide, acute apex, entire margin, smooth texture, upper and lower surfaces are rose (RHS Red-Purple Group 65C) aging to taupe (RHS Greyed-Orange Group 164C) then to medium brown (RHS Greyed-Orange Group 164A).

*Stamens.*—Filaments are typically 2.5 mm high and 0.5 mm wide, pale flesh-colored (RHS Orange-White Group 159C), anthers are typically 1 mm high and 1 mm wide, colored fleshy red (RHS Greyed-Red Group 179B) turning brown (RHS Brown Group 200C).

*Pistil.*—Typical 2 mm high and 1 mm wide, colored a light, but bright green (RHS Green Group 141D).

*Peduncle.*—Typical 2 mm high and 0.5 mm wide, colored pale green (RHS Yellow-Green Group 145C).

*Pollen.*—Typical size of 225 grains per square millimeter, colored pale yellow (RHS Green-Yellow Group 1D).

*Season.*—Early September in Monroe, Ga., Zone 7b.

*Fragrance.*—None.

Fruit:

*Type.*—Samara, flat, ovate to obovate, containing one flat seed.

*Color.*—Green (RHS Green Group 137A) aging to brown (RHS Greyed-Orange Group 165B).

*Size.*—Typically, 8 mm long, 6 mm wide, 1 mm thick.

*Season.*—Late September through October in Monroe, Ga., Zone 7b.

Disease and pest resistance: Highly resistant to Dutch Elm Disease and Elm Leaf Beetle damage. There have been no symptoms of scorch in drought years. The tree has proven resistant to wind and ice damage.

Winter hardiness: Not yet determined, due to only being grown and observed in Monroe, Ga. (USDA Zone 7b).

I claim:

1. A new and distinct variety of Chinese Elm tree named 'BSNUPF,' substantially as herein illustrated and described, characterized particularly as to novelty by its tight upright narrow growth, tight branches, and ornamental bark that exfoliates in patches to provide patch marks of different colors.

* * * * *